United States Patent [19]
Nishikawa

[11] 4,256,402
[45] Mar. 17, 1981

[54] METHOD AND APPARATUS OF DETECTING TONER CONCENTRATION OF DRY DEVELOPER

[75] Inventor: Masaji Nishikawa, Hachioji, Japan

[73] Assignee: Olympus Optical Co. Ltd., Tokyo, Japan

[21] Appl. No.: 936,081

[22] Filed: Aug. 23, 1978

[30] Foreign Application Priority Data

Sep. 1, 1977 [JP] Japan ................................ 52/104159

[51] Int. Cl.³ ...................... G01N 33/28; G01N 21/55; G03G 15/00

[52] U.S. Cl. ...................................... 356/38; 356/445; 356/440; 355/3 DD; 118/691

[58] Field of Search ............ 355/3 DD; 118/689, 690, 118/691, 653; 222/DIG. 1; 356/38, 440, 445; 250/576

[56] References Cited

U.S. PATENT DOCUMENTS

| | | | |
|---|---|---|---|
| 2,951,443 | 9/1960 | Byrne | 430/126 |
| 3,376,854 | 4/1968 | Kamola | 118/691 |
| 3,430,606 | 3/1969 | Pease et al. | 118/691 |
| 3,526,338 | 9/1970 | Goodrich et al. | 222/1 |
| 3,527,387 | 9/1970 | Wilson | 222/57 |
| 3,553,464 | 1/1971 | Abe | 118/691 |
| 3,604,939 | 9/1971 | Maksymiak | 250/218 |
| 3,635,373 | 1/1972 | Kuhl et al. | 222/57 |
| 3,754,821 | 8/1973 | Whited | 355/4 |
| 3,777,173 | 12/1973 | Landrith | 250/575 |
| 3,791,744 | 2/1974 | Erny et al. | 356/201 |
| 3,870,197 | 3/1975 | Landrith | 222/DIG. 1 |

OTHER PUBLICATIONS

Smith, Toner Concentration Control, Apr. 1977, IBM Technical Disclosure Bulletin.

*Primary Examiner*—Vincent P. McGraw
*Assistant Examiner*—Rodney B. Bovernick
*Attorney, Agent, or Firm*—Weinstein & Sutton

[57] ABSTRACT

A method and apparatus to detect the toner concentration of two component dry developer comprising toner and carrier includes the use of a toner catcher having a conductive member and which is capacitively charged. The developer is applied to the catcher, which traps the toner to determine the toner content.

13 Claims, No Drawings

METHOD AND APPARATUS OF DETECTING TONER CONCENTRATION OF DRY DEVELOPER

BACKGROUND OF THE INVENTION

The invention relates to a method of detecting the toner concentration of two component dry developer which is used in the developing of an electrostatic latent image, and an apparatus used to carry out the method.

An electrostatic latent image is converted into a visual image by using two component developer. To this end, toner and carrier are intermixed and rubbed against each other to charge the toner to a polarity which is opposite to the polarity of charge which forms an electrostatic latent image. Coulomb force acting between the toner and carrier causes the toner to be attached to the carrier, and the developer under this condition is applied to a surface to be developed. Carrier usually comprises glass beads, magnetic powder or the like while the toner comprises heat sensitive, pressure sensitive or solvent gas sensitive resin powder containing a color pigment. The purpose of using the carrier in the developer is to prevent a photographic fog in a non-image region by the Coulomb force which pulls the toner portion attaching to non-image regions back to the carrier. In addition, the application of the carrier to the surface to be developed achieves a uniform attachment of a suitable concentration of toner to the surface.

In a known electrophotographic apparatus which utilizes the aforementioned dry developer, it is readily apparent that a varying toner concentration or content of the developer results in a change in the optical density of the image formed on a copy. An electrophotographic process to obtain a plurality of copies by repeating the developing of an electrostatic latent image and the transfer of the developed image onto a transfer sheet is disclosed in U.S. Pat. No. 2,951,443, as well as other patents. To enable the number of copies to be produced without noticeable degradation in the image quality, it is necessary to avoid the erasure of the latent image during the developing step. This can be achieved by increasing the toner concentration where a semi-conductive carrier such as magnetic powder is used. However, an excessively high toner concentration causes a fog to be produced in non-image regions and also causes a reduced flowability of the developer. Thus a control of the toner concentration is required. It is experimentarily established that for a developer including the iron powder carrier having a resistivity on the order of $1\times10^6$ to $1\times10^8\Omega$ cm, a toner concentration in the range from 4 to 15% by weight is satisfactory.

To achieve a proper control of toner concentration, a variety of methods and apparatus have been proposed which detect the toner concentration of a developer contained in a developer vessel to supply toner or developer from time to time in order to maintain a proper value of toner concentration. The detection can be accomplished in two ways. A first technique utilizes the detection of a change in the physical properties of the developer such as color, specific gravity, permeability, dielectric constant, resistance or the like. However, a change in these properties is minimal as compared with a corresponding change in the toner concentration, and hence the resulting signal suffers from a poor S/N ratio. This disadvantageously necessitates a complex and expensive detection arrangement.

Another detection technique employs the optical determination of the toner quantity on a detecting surface which is developed with the developer. The detecting surface may comprise a charged insulating layer or an electrically energized conductive member. An example of the former is a detecting tape which is subjected to corona charging before the developing takes place. The required arrangement is complex and requires an extensive space to permit the deployment of the tape. As a further example, an apparatus is known which regulates the optical density of an image. With this apparatus, a developed image on a photosensitive drum is optically scanned, and a signal indicative of the maximum optical density is used to control the toner concentration. This requires a complicated instrumentation circuit, and it is believed that control parameters must be varied in accordance with an original. Hence, this approach leads to a complex control of the toner concentration. The latter approach is exemplified by U.S. Pat. Nos. 3,376,854, No. 3,430,606, No. 3,526,338, No. 3,527,387, No. 3,604,939, No. 3,635,373, and No. 3,754,821. However, from experiments which will be described later, it is found that when the developing is effected with a voltage applied to the conductive member, the saturation density rises to a substantially high value independently of the toner concentration, rendering it difficult to detect and control the toner concentration with an effective accuracy.

Other examples of the latter approach are given in U.S. Pat. No. 3,777,173 and No. 3,791,744. Essentially, these patents describe a process in which a developer including a glass bead carrier is used to effect a cascade developing of a toner catcher plate, and the concentration of toner trapper by the plate is determined. No positive means is provided which applies an electrical influence upon the catcher plate to trap the toner. This approach is inapplicable to an apparatus which incorporates a magnet brush developing system since it is directed to a cascade developing of the catcher plate.

SUMMARY OF THE INVENTION

It is a first object of the invention to provide a method of detecting the toner concentration of two component dry developer with a high accuracy while eliminating the described disadvantages of the prior art.

It is a second object of the invention to provide an apparatus which is optimally adapted to carry out the method of the invention.

In accordance with the invention, the toner concentration can be detected with a high accuracy by developing a toner catcher which is capacitively charged with a developer, and determining the developed density of the catcher to provide an indication of the toner concentration. The indication can be relied upon in controlling the supply of toner in order to maintain a proper toner concentration. The apparatus which is used to carry out the method requires no special space since a charged conductive member can be disposed in a region adjacent to a developer vessel where it is susceptible to developing by the developer.

BRIEF DESCRIPTION OF THE DRAWINGS

FIG. 1 is a schematic view illustrating the principle of the invention;

FIG. 2 is a perspective view of a toner catcher used in the method of the invention;

FIGS. 3A, B and C graphically show the experimental results obtained with the toner catcher of FIG. 2, plotting the developed density against the applied voltage;

FIG. 4 is a schematic cross-section of an apparatus according to one embodiment of the invention;

FIG. 5 is a fragmentary cross-section of another form of toner concentration detector, together with a wiring diagram;

FIG. 6 is a circuit diagram of a charging circuit associated with the toner catcher;

FIG. 7 is a cross-section of another form of toner catcher;

FIG. 8 is a circuit diagram of another charging circuit;

FIG. 9 is a cross-section of a further form of toner catcher;

FIG. 10A is a cross-section of still another form of toner catcher; and

FIG. 10B is a graph depicting the concentration signal obtained with the toner catcher of FIG. 10A.

DESCRIPTION OF PREFERRED EMBODIMENTS

FIG. 1 schematically illustrates the principle of the invention. Conductive plate 1 is connected with the ground through capacitor 2, which is adapted to be charged from a d.c. source 3 connected therewith through switch 4. The developing unit is disposed below the conductive plate 1, and typically comprises a magnet roller developing unit including magnet roller 5 located opposite to conductive plate 1 and connected with the ground. A quantity of dry developer 6 is distributed around the roller 5. In operation, switch 4 is turned on for a short interval to charge capacitor 2. It is desirable that the charging step be completed when conductive plate 1 is located out of the developing effect or within a time period which is short enough to prevent any developing effect. Charge stored across capacitor 2 is transferred to conductive plate 1, which therefore attracts toner contained in the developer 6. Charge continues to be supplied from capacitor 2 as toner is attracted to conductive plate 1, and when a developing takes place over a prolonged period of time, toner is trapped by conductive plate 1 in an amount which corresponds to the magnitude of charge stored across capacitor 2. The amount of trapped toner is determined by photoelectric means to provide an indication of the toner concentration of developer 6. It is believed that as the toner concentration of developer 6 increases, there is an increased quantity of toner which is freed from the toner carrier, i.e., a force of less magnitude is sufficient to separate toner from carrier. Thus when the capacitance of capacitor 2, the voltage of source 3 and the developing period are fixed, a change in the toner concentration can be detected with a degree of high accuracy.

An experiment has been conducted by developing conductive plate 1 while maintaining switch 4 closed. Then a large quantity of toner is rapidly deposited on conductive plate 1, resulting in a failure to detect a differential toner concentration. The same holds true if the capacitance of capacitor 2 or the voltage of source 3 is varied. Thus it is concluded that the toner concentration cannot be effectively detected with the process disclosed in U.S. Pat. No. 3,376,854 unless the described problem is overcome.

FIG. 2 shows one form of toner catcher 7 used in the method of the invention. Toner catcher 7 comprises conductive base 8, insulating layer 9 and conductive surface layer 10 in laminated form. Catcher 7 functions as capacitor 2 shown in FIG. 1 and traps toner on its surface layer 10, which constitutes a conductive member. The capacitance of catcher 7 can be adjusted by varying the thickness of insulating layer 9 or alternatively by connecting additional capacitor 11 in shunt or series with toner catcher 7.

FIGS. 3A, B and C graphically show the results of experiments obtained with the toner catcher 7 shown in FIG. 2, illustrating the developed saturation density D on the ordinate plotted against the applied voltage V shown on the abscissa. Three models of toner catcher have been used having capacitance per square centimeter of 25, 50 and 100 pF, respectively. They are charged for a given interval to varying voltages, and are then manually developed by moving a magnet carrying developer thereon close to them and maintaining the magnet in position for a sufficient period of time. One developer comprises iron powder carrier and 3% by weight of toner (corresponding curves shown in dotted lines), another developer comprises 10% by weight of toner (shown in solid line). In these Figures, it is noted that the developed density for the 3% toner concentration varies with both the applied voltage and the capacitance. Differences which occur with a change in the toner concentration are seen from solid line and dotted line curves shown in FIGS. 3A and B. It will be noted that there is a difference in the fog density which prevails at zero applied voltage. Thus a fog density can be utilized where it is desired to detect a change in the toner concentration at a relatively high level. To prevent a triboelectric charging between developer and toner catcher, it is advantageous to develop the surface layer of the toner catcher as mentioned.

As will be evident from FIG. 3, a suitable combination of the capacitance of the toner catcher and the applied voltage depends on the level of toner concentration to be controlled, but it will be noted that a high capacitance is advantageous for a low toner concentration while a low capacitance is advantageous for a high toner concentration. A higher value is preferred for the applied voltage, which is determined in connection with the response of a concentration detector. This is because if a photoelectric determination of the density is utilized, it is possible that the photoelectric output may be reduced to degrade S/N ratio if there is sufficient density differential in a region of higher optical density, thus resulting in a failure to detect the density differential. A signal indicative of the toner concentration can be used to control a toner supply mechanism so that a proper toner concentration can be maintained in the developing unit.

The saturation developed density varies with the toner concentration because the quantity of toner which attaches to carrier varies an mentioned previously. Specifically, if the charge on the toner catcher is held constant, there will be a balance reached between the toner quantity which is attracted to the surface layer under the influence of electrostatic interaction and the toner quantity which is removed or scraped off as a result of rubbing against the carrier, the balance value being dependent on the degree of toner attachment to the carrier. In other words, a saturation will be reached with a quantity of toner which is less than that which attaches under the electrostatic force. As a consequence, the saturation developed density varies with the toner concentration.

FIG. 4 shows an apparatus for detecting the toner concentration which is constructed according to one embodiment of the invention. The apparatus is used with an electrophotographic apparatus which includes developing drum 12 comprising a conductive drum which is peripherally provided with a photosensitive layer. An electrostatic latent image is formed on the drum and developed and thereafter transferred onto a transfer sheet to provide a copy during the rotation of the drum. Developing unit 13 is located adjacent to the periphery of drum 12, and comprises magnet roller 16 which carries and retains thereon developer 15 from vessel 14, agitator blades 17, and toner supply 18. Toner supply 18 includes hopper 20 which contains a quantity of toner 19, and peripherally knurled roller 21 disposed below the bottom opening of hopper 20. Roller 21 responds to a toner supply command, to be described later, by rotating to supply or replenish toner 19 from hopper 20 to vessel 14.

In accordance with the invention, drum-shaped toner catcher 22 is disposed adjacent to magnet roller 16. In the example shown, toner catcher 22 comprises conductive roller 23 which is peripherally coated with insulating layer 24, on top of which conductive surface layer 25 is applied. Surface layer 25 is divided into three segments which are electrically connected with three corresponding slip rings 26 mounted on the rotating shaft of conductive roller 23 with suitable insulation interposed therebetween. Where an adjustment of the capacitance of catcher 22 is desired, additonal capacitors may be connected between surface layer 25 and conductive roller 23 as indicated by phantom lines. Sliding brush 27 is disposed for contact with the three slip rings 26. A d.c. source 28 is connected between conductive roller 23 and brush 27 to permit a charging of insulating layer 24 in its region located between conductive roller 23 and that surface layer segment 25 which is connected with a particular slip ring 26 which engages the brush 27. The brush 27 is located such that a segment of surface layer 25 which is postioned for contact with developer 15 cannot be energized. In the present embodiment, conductive roller 23 is electrically connected with magnet roller 16 so as to assume an equal potential. The conductive drum of developing drum 12 may also be at the same potential as these rollers, but a source of variable developing bias 29 is connected therebetween in the embodiment shown. Optical density detector 30 is disposed in the vicinity of catcher 22 in order to determine the quantity of toner that is trapped on the surface layer 25. It comprises light source 31, condenser lens system 32 and light receiver 33.

Conductive roller 23 is driven, by drive means not shown, for rotation in a given direction at a uniform rate in integral manner with the slip rings 26, and hence toner catcher 22 experiences one cycle of charging, developing and toner concentration detection during its one revolution. Detector 30 produces a signal indicative of the toner concentration, which selectively activates toner supply 18. If the detector 30 detects a toner concentration below an optimum value, it directs a toner supply command to the toner supply 18. In response thereto, roller 21 rotates to supply toner 19 from hopper 20 to vessel 14. In this manner, a desired toner concentration can be maintained within the vessel 14.

FIG. 5 shows another embodiment in which surface layer 25 is not divided into three segments as in FIG. 4, but is a continuous conductive surface layer 25A. In this embodiment, toner catcher 22 is charged by turning switch 34 on for a short interval during the developing step. Toner catcher 22 may be rotated by friction with developer 15. However, if the rate of rotation thus achieved is unsatifactory and a sufficient developing period cannot be assured, an arrangement as shown in FIG. 5 may be used. As shown, cam disc 35 is mounted on the rotating shaft 23*a* of conductive roller 23 for engagement with stop 36. The stop 36 may be moved to the disengaged position by the action of solenoid 37 to permit an intermittent rotation of toner catcher 22 so that sufficient developing period can be assured.

FIG. 6 shows a circuit diagram of a charging circuit for toner catcher 22. In this instance, the toner catcher 22 shown in FIG. 5 is employed. A series combination of normally open switch 38 and resistor 39 is connected between conductive roller 23 and surface layer 25A. A single pole double throw switch 40 has its movable contact connected for ganged movement with switch 38 and is normally thrown to contact 40*a* which connects charging capacitor 41 across roller 23 and layer 25A. Source 28 is connected with the other contact 40*b* of switch 40 and with roller 23.

In operation, when switch 38 is closed, switch 40 is changed to the other contact 40*b*, whereby capacitor 41 is connected with and charged by source 28. The closure of switch 38 causes a discharge of toner catcher 22 through resistor 39. Subsequently when switch 40 is switched again, capacitor 41 acts as a secondary power source to charge toner catcher 22, thus enabling toner to be trapped by surface layer 25A. The use of capacitor 41 avoids an excessive power dissipation. The provision of resistor 39 prevents an instantaneous discharge of capacitor 41 which might otherwise occur as a result of a mismatched switching of switches 38,40 such that switch 38 remains closed when the movable contact of switch 40 is thrown to contact 40*a*. Nevertheless, the presence of resistor 38 does not pose any problem when toner catcher 22 is to be discharged since certain time allowance is possible. However, it will be understood that resistor 39 can be dispensed with if switches 38, 40 are separately controlled.

FIG. 7 shows a further form of toner catcher. In this instance, toner catcher 22 comprises rockable conductive arm 42 having arcuate free and 42*a* on which insulating layer 24 and conductive surface layer 25 are sequentially laminated. Toner catcher 22 is developed while it is located adjacent to magnet roller 16, and is then rocked to position 42A shown in phantom lines where optical concentration detector 30 operates to detect the quantity of toner trapped on the surface layer 25. This arrangement can be used with any one of the charging circuits shown in FIGS. 4 to 6.

FIG. 8 shows still another form of charging circuit. Here, a separate capacitor 43 is connected between conductive roller 23 and surface layer 25 of toner catcher 22 and is also connected with source 28 through a series combination of power switch 34 and polarity reversal switch 44 so as to apply a voltage of either polarity across the toner catcher 22. This permits the surface layer 25 to repel toner which has attached thereto, thus increasing the accuracy and response rate of detection. Where such repellent is unavailable, toner is removed from toner catcher 22 by carrier through a slow process.

FIG. 9 shows another form of toner catcher which simply comprises conductive roller 23 alone. Since no charge can be stored on catcher roller 23 itself, capacitor 45 is connected between conductive roller 23 and magnet roller 16 to provide the charge storing capability. The charging circuit of FIG. 9 is similarly constructed as shown in FIG. 8, but may be replaced by any one of the circuits shown in FIGS. 4 to 6. The configuration of toner catcher 22 need not be a drum.

FIG. 10 shows an alternative form of toner catcher. It comprises conductive roller 23, insulating layer 24 which is laminated thereon, and an array of alternately disposed conductive surface layers 25 and grounded conductive layers 46. Surface layer 25 is adapted to be charged while grounded layer 46 is maintained at the ground potential in order to provide a correction of fogging density. With this toner catcher, a developed density corresponding to the applied voltage is detected on surface layer 25 while a fogging density is detected on the grounded layer 46. If a single optical density detector is used with this toner catcher, it will produce a signal a shown in FIG. 10B, which enables a change in the toner concentration to be detected from a change in the difference between the developed density and the fogging density. It is to be understood that a pair of toner catchers may be provided, one having a charged surface layer and the other having a grounded conductive layer, for cooperation with separate optical density detectors which detect the developed density and the fogging density, respectively.

It is to be noted that in the described embodiments, means disclosed in connection with a particular embodiment can also be used in another embodiment. As a modification, an experiment has been conducted to effect the developing while applying an a.c. voltage to toner catcher 22. A pattern corresponding to the a.c wave is developed on the catcher. It is found that the density of the pattern is not significantly influenced by the magnitude of the a.c. voltage applied, but that the pitch of the undulating pattern varies with the speed of movement of the magnetic brush or the carrier which attaches to the magnet roller 16 in the form of tuft. This indicates that the attachment and the separation of toner takes place at a relatively high rate. The average value of the toner concentration was close to a fogging density, and hence it is found possible to detect the toner concentration with this technique since the fogging density corresponds to the toner concentration.

It is to be understood that the invention is not limited to the embodiments described above, and that a number of changes and modifications can be made therein. By way of example, the optical density can be detected by means other than the photoelectric detector described, as by the determination of the resistance or charge of trapped toner. In addition, the conductive member of the toner catcher on which toner is trapped may be coated with a very thin insulating layer for purpose of protection. Furthermore, the invention is not limited to its use in an electrophotographic apparatus, but is equally applicable to other systems such as facsimile system in which an electrostatic latent image formed is developed with two component dry developer. Finally, though toner catcher is shown in a rotating drum configuration in FIGS. 4 to 10A, it may be shaped as a flat plate for cascade developing or shaped into any other form combined with a suitable developing process.

What is claimed is:

1. In a toner concentration determining apparatus including an electrically chargeable conductive member which, when charged, attracts toner from dry developer, including said toner and carrier, the improvement comprising at least one capacitor, means for charging said capacitor with a predetermined quantity of electric charge, means for transferring said predetermined quantity of electric charge of said capacitor to said conductive member, the predetermined quantity of electric charge of said conductive member having a magnitude and polarity selected such that said charged conductive member attracts said toner from said dry developer in an amount representative ot the toner concentration thereof.

2. An apparatus according to claim 1 in which the conductive member comprises a conductive base, an electrically insulating layer and a conductive surface layer which are sequentially laminated together.

3. An apparatus according to claim 1 in which the conductive member comprises a conductive roller, an electrically insulating layer laminated on the outer periphery of the conductive roller, and a conductive surface layer laminated on the insulating layer, the conductive member being driven for rotation in a given direction and at a uniform rate.

4. An apparatus according to claim 1 in which the conductive member comprises a conductive roller, an array of electrically insulating layers and grounded conductive layers on the roller which are arranged in alternating fashion about the circumference of the roller, the grounded layers being maintained at ground potential to provide a correction of a fogging density, and a plurality of conductive surface layers on each of the insulating layers.

5. An apparatus according to claim 1, further comprising means for determining the amount of toner attracted to the conductive member, the determining means including an optical density detector having a light source, a lens system and a light receiver.

6. The apparatus of claim 1, further comprising a receptacle for containing dry developer from which dry developer is conveyed to the conductive member ;

means for determining the amount of toner attracted to the conductive member, said amount of toner corresponding to the toner concentration of the developer;

a supply source of fresh dry developer and means responsive to said determining means for dispensing fresh dry developer from said supply source into said receptacle when said concentration falls below a predetermined level.

7. An apparatus according to claim 1, in which the conductive member is mounted at a free end of a rockable arm , the conductive member having an arcuate surface, an electrically insulating layer and a conductive surface layer, the electrically insulating layer and the conductive surface layer being respectively laminated on the arcuate surface of the conductive member.

8. An apparatus according to claim 7 which the conductive member is movable between a first position where the toner is attracted thereto and a second position where the amount of the attracted toner is determined.

9. An apparatus according to claim 1, in which the means for charging said capacitor includes a d.c. source, the conductive member comprising a conductive base, an electrically insulating layer and a conductive surface layer, the source being connected between the conductive base and the surface layer to charge the insulating layer.

10. An apparatus according to claim 8 in which the capacitance of the conductive member is adjusted by connecting an additional capacitor between the conductive base and the surface layer.

11. An apparatus according to claim 9 in which the d.c. source is connected between the conductive base and the surface layer through a power switch and a polarity reversal switch.

12. An apparatus according to claim 1, further comprising a magnetic roller which is disposed within a vessel which contains the developer, the magnetic roller being located in close proximity to the conductive member whereby the conductive member attracts said toner from the magnetic roller which carries the dry developer and also supplies it to a developing drum.

13. In a method of determining the toner concentration of dry developer, including toner and carrier, by electrically charging a conductive member so as to attract toner from dry developer, the improvement comprising the steps of charging a capacitor with a predetermined quantity of electric charge, transferring the charge of said capacitor to said conductive member, selecting the magnitude and polarity of said charge such that said charged conductive member attracts said toner from said dry developer in an amount representative of the toner concentration thereof.

* * * * *

UNITED STATES PATENT AND TRADEMARK OFFICE

CERTIFICATE OF CORRECTION

PATENT NO. : 4,256,402

DATED : March 17, 1981

INVENTOR(S) : Masaji Nishikawa

It is certified that error appears in the above—identified patent and that said Letters Patent is hereby corrected as shown below:

On the title page "No Drawings" should read -- 13 Drawing Figures ---.

Figures 1-10(B) should be added as shown on the attached sheets.

Signed and Sealed this

*Third* Day of *November 1981*

[SEAL]

*Attest:*

GERALD J. MOSSINGHOFF

*Attesting Officer* *Commissioner of Patents and Trademarks*

UNITED STATES PATENT AND TRADEMARK OFFICE

CERTIFICATE OF CORRECTION

PATENT NO. : 4,256,402

DATED : March 17, 1981

INVENTOR(S) : Masaji Nishikawa

It is certified that error appears in the above—identified patent and that said Letters Patent is hereby corrected as shown below:

F I G. 1

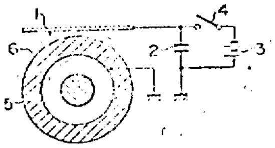

F I G. 2

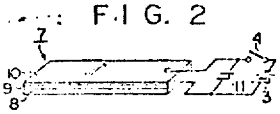

F I G. 3(A)

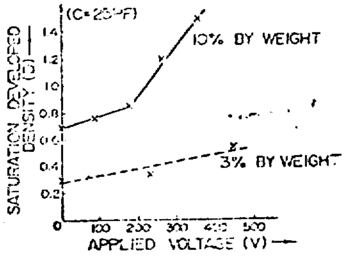

F I G. 3(B)

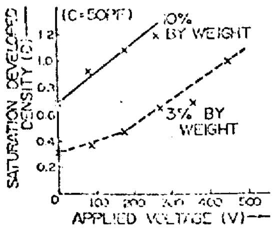

F I G. 3(C)

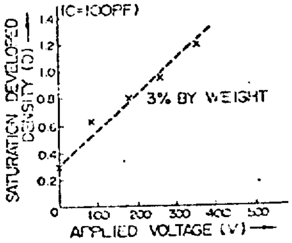

UNITED STATES PATENT AND TRADEMARK OFFICE
CERTIFICATE OF CORRECTION

PATENT NO. : 4,256,402

DATED : March 17, 1981

INVENTOR(S) : Masaju Nishikawa

It is certified that error appears in the above—identified patent and that said Letters Patent is hereby corrected as shown below:

F I G. 4

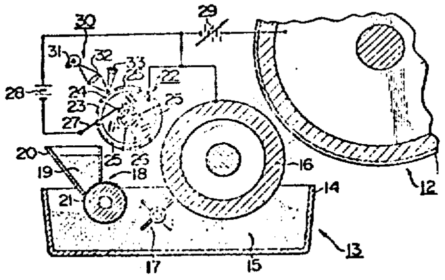

F I G. 5

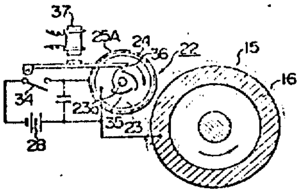

F I G. 6

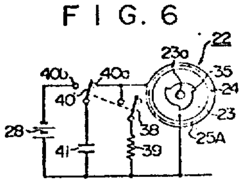

UNITED STATES PATENT AND TRADEMARK OFFICE
CERTIFICATE OF CORRECTION

PATENT NO. : 4,256,402

DATED : March 17, 1981

INVENTOR(S) : Masaji Nishikawa

It is certified that error appears in the above—identified patent and that said Letters Patent is hereby corrected as shown below:

F I G. 7

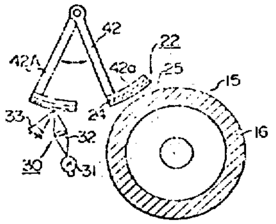

F I G. 8

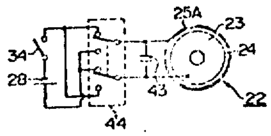

F I G. 9

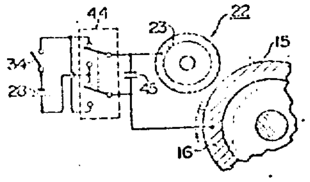

F I G. 10(A)

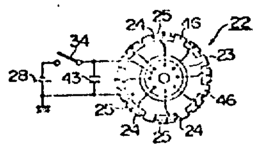

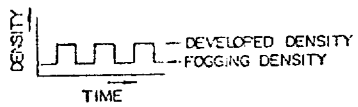

F I G. 10(B)